United States Patent [19]

Young

[11] 3,987,009

[45] Oct. 19, 1976

[54] TRANSITION METAL CATALYST COMPOSITIONS

[75] Inventor: Frank G. Young, Charleston, W. Va.

[73] Assignee: Union Carbide Corporation, New York, N.Y.

[22] Filed: Dec. 12, 1974

[21] Appl. No.: 532,211

Related U.S. Application Data

[63] Continuation of Ser. No. 263,231, June 15, 1972, abandoned.

[52] U.S. Cl. .................. 260/46.5 E; 252/429 R; 252/431 C; 252/431 N; 252/431 P; 260/46.5 G; 260/448.2 N
[51] Int. Cl.² .................................. C08G 77/04
[58] Field of Search ........ 252/429 R, 431 C, 431 N, 252/431 P; 260/46.5 E, 46.5 G, 448.2 N

[56] References Cited
UNITED STATES PATENTS

| | | | |
|---|---|---|---|
| 2,995,594 | 8/1961 | Fekete | 260/448.8 |
| 3,019,248 | 1/1962 | Fekete | 260/448.8 |
| 3,726,809 | 4/1973 | Allum et al. | 252/431 P |

FOREIGN PATENTS OR APPLICATIONS

| | | | |
|---|---|---|---|
| 2,062,351 | 6/1971 | Germany | 260/46.5 E |

*Primary Examiner*—Lewis T. Jacobs
*Attorney, Agent, or Firm*—Bernard Lieberman

[57] ABSTRACT

A catalyst composition consisting essentially of a non-linear polymer consisting essentially of a recurring unit having the following structural formula:

$$(R^2)_2P-R^1-Si-O_{3/2}$$

wherein $R^1$ is an unsubstituted or substituted straight or branched chain divalent saturated alkylene radical having 1 to 10 carbon atoms or an unsubstituted or substituted divalent aryl radical having 1 to 3 benzene rings wherein the substituents for the alkylene radical can be halogen or a phenyl radical and the substituents for the aryl radical can be halogen or straight or branched chain saturated alkyl radicals having 1 to 5 carbon atoms; and $R^2$ is an unsubstituted or substituted straight or branched chain or cyclic monovalent saturated alkyl radical having 1 to 10 carbon atoms or an unsubstituted or substituted monovalent aryl radical having 1 to 3 benzene rings wherein the substituents for the alkyl radical can be halogen or a phenyl radical and the substituents for the aryl radical can be halogen or straight or branched chain saturated alkyl radicals having 1 to 5 carbon atoms; and wherein each phosphorous atom in the polymer is coordinated with a platinum or palladium metal atom having a zero or positive charge, each positively charged metal atom having a sufficient number of negatively charged organic or inorganic radicals, devoid of functional groups, attached thereto to satisfy the valence of said transition metal atom, and wherein the radicals are selected from the group consisting of halogens; nitrates; sulfates; straight chain alkoxy or acyloxy radicals having 1 to 10 carbon atoms; and aryloxy radicals having 1 to 3 benzene rings.

5 Claims, No Drawings

TRANSITION METAL CATALYST COMPOSITIONS

This is a continuation of application Ser. No. 263,231 filed June 15, 1972 and now abandoned.

FIELD OF THE INVENTION

This invention relates to transition metal catalyst compositions adapted for use in heterogeneous catalysis and precursors therefor.

DESCRIPTION OF THE PRIOR ART

Homogeneous catalysis in chemical synthesis is an important development in industrial chemistry. The processes of chemical synthesis in which this type of catalysis is common depend on the use of transistion metals coordinated to various electron-donor ligands and are operated in solution. Some of the important homogeneous catalytic processes that have been commercialized and the transition metals commonly used therein are the OXO process (cobalt, rhodium), acetic acid from methanol (rhodium), acetaldehyde from ethylene (palladium), propylene oxide by hydroperoxide oxidation (molybdenum, vanadium), vinyl chloride and vinyl acetate from ethylene (copper), phenol from toluene via benzoic acid (copper), hydrogenations (platinum, palladium, cobalt), olefin dismutation (tungsten), and oxidation processes (nickel, copper).

One feature that these processes involving homogeneous catalysis have in common is that they make use of a relatively expensive metal compound as a catalyst. To be economical, the processes must use the metal effectively. This is generally accomplished by achieving very high catalyst productivity (high turnover), by eliminating or substantially reducing catalyst losses, and by recovering the spent metal cheaply and efficiently. To improve the economics of the aforementioned processes while maintaining catalyst productivity at a high level, industrial research in the field of catalysis has attempted to either substitute heterogeneous catalysts for the homogeneous catalysts used heretofore or improve on known processes for recovery of the spent metal. While improvements have been forthcoming from time to time, optimization along either line has proved elusive.

SUMMARY OF THE INVENTION

An object of the invention, therefore, is to provide a transition metal catalyst composition, which, while maintaining high productivity, can be used in heterogeneous catalysis rather than homogeneous catalysis thus substantially reducing catalyst losses, and precursors therefor, or, in the alternative, providing compositions in the form of one of said precursors which can be used to recover spent metal employed in homogeneous catalysis.

Other objects and advantages will become apparent hereinafter.

According to the present invention, a high productivity catalyst composition has been discovered consisting essentially of a non-linear polymer consisting essentially of a recurring unit having the following structural formula:

$(R^2)_2P-R^1-Si-O_{3/2}$ wherein $R^1$ is an unsubstituted or substituted straight or branched chain divalent saturated alkylene radical having 1 to 10 carbon atoms or an unsubstituted or substituted divalent aryl radical having 1 to 3 benzene rings wherein the substituents for the alkylene radical can be halogen or a phenyl radical and the substituents for the aryl radical can be halogen or straight or branched chain saturated alkyl radicals having 1 to 5 carbon atoms; and $R^2$ is an unsubstituted or substituted straight or branched chain or cyclic monovalent saturated alkyl radical having 1 to 10 carbon atoms or an unsubstituted or substituted monovalent aryl radical having 1 to 3 benzene rings wherein the substituents for the alkyl radical can be halogen or a phenyl radical and the substituents for the aryl radical can be halogen or straight or branched chain saturated alkyl radicals having 1 to 5 carbon atoms; and wherein each phosphorus atom in the polymer is coordinated with a platinum or palladium metal atom having a zero or positive charge, each positively charged metal atom having a sufficient number of negatively charged organic or inorganic radicals, devoid of functional groups, attached thereto to satisfy the valence of said transition metal atom, and wherein the radicals are selected from the group consisting of halogens; nitrates; sulfates; straight chain alkoxy or acyloxy radicals having 1 to 10 carbon atoms; and aryloxy radicals having 1 to 3 benzene rings.

DESCRIPTION OF THE PREFERRED EMBODIMENT

Reference will be made throughout to the Periodic Table, transition elements (or metals), and oxidation states. These references are based on the Periodic Table of the Elements found on the inside of the back cover of the Handbook of Chemistry and Physics, 46th Edition, published by The Chemical Rubber Co., 1965, said Periodic Table being incorporated by reference herein.

It will be understood that the processes for preparing first and second precursors, and the ultimate catalyst are conventional; however, there is no generic process for preparing each first precursor. Various processes, will, therefore, be suggested by way of example, all of which are satisfactory for making at least some of the species which fall within the recited generic formulae.

Two general approaches to the synthesis of the first catalyst precursor, $(RO)_3-Si-R^1-P-(R^2)_2$, can be taken. The first involves the formation of, e.g., functionalized diphenylphosphine, which is then coupled to a silane; the second is the reverse process, i.e., first functionalizing a silicon derivative, then linking it to, e.g., a diphenylphosphine group.

The second catalyst precursor, a polymer consisting essentially of a recurring unit having the following structural formula:

$(R^2)_2P-R^1-Si-O_{3/2}$ may be called a poly-silsequioxane (the unit may be called a silsesquioxane), is prepared by conventional hydrolysis of the first precursor. Hydrolysis can be accomplished by simply admixing the first precursor with water and heating at temperatures in the range of about 25° C. to about 200° C. at atmospheric or higher pressures. Refluxing the mixture is a practical way of accomplishing this. Other mediums of hydrolysis can be used such as water containing acids or alkalies, and polar organic solvents containing dissolved water, acids, or bases. The resulting polymer is generally a glassy infusible solid melting above 300° C., insoluble in most of the common solvents, but soluble in acetone, dimethylformamide, and dimethylsulfoxide. It has a decided degree of thermal stability in the 300° C. to 350° C. range, but tends to get sticky at those temperatures. For this reason, and also because of caking in the presence of some active solvents, the polymer can be diluted with a silica gel or crosslinked by cohydrolysis of the first precursor with, e.g., tetrafunctional silicate esters. Theoretically, end-blocking is accomplished by the hydrolyzable R radical defined heretofore; however, these radicals are difficult to distinguish by analysis especially in the polymers of higher molecular weight. The non-linearity of the polymer contributes to this difficulty, which is compounded when cross-linking agents are used. Crosslinking will be discussed further hereinafter.

The catalyst is synthesized by introducing a suspension of the second precursor, i.e., the polymer, in a medium such as methanol into a solution of a transition metal salt, e.g., platinic chloride hexahydrate dissolved in methanol. The metal atoms coordinate with the phosphorus atoms of the precursor and a complex is formed which can be used in heterogeneous catalysis. In the alternative, the same suspension of second precursor can be introduced into a solution containing a spent homogeneous catalyst composition similar to the transition metal salt mentioned heretofore dissolved in water or alcohol. Again, complexing occurs and the platinum coordinates with the phosphorus in the same manner. Since transition metals have from one to six coordination sites it is clear that one transition metal atom can coordinate with one to six phosphorus atoms or one to six of the repeating units of the polymer. In the alternative case, the transition metal can be recovered by displacement from the acid or by other conventional means or the complex can be used in heterogeneous catalysis. Where a heterogeneous catalyst is desired, simple decantation is all that is necessary to separate the catalyst composition formed in this way.

An example of a complex formed by the reaction of sodium chloropalladite with polydiphenylphosphinylethylsilsesquioxane containing 5 recurring units can be represented as follows:

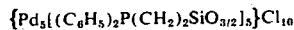

and a complex formed similarly using sodium chloroplatinite can be represented in the same manner by simply substituting platinum for palladium in the above formula.

Returning to the structural formulas recited heretofore:

R can be any organic, organometallic, or inorganic radical selectively hydrolyzable at the R—O bond wherein the organic and organometallic radicals are monovalent and the inorganic radical is in an oxidation state of +1, said radicals having 1 to 25 atoms in their molecular structure and being devoid of functional groups, which would inhibit hydrolysis at the R—O bond or react with phosphorus. The only R radicals which may remain in the second precursor and the catalyst are those in endblocking positions. The balance of the R radicals are, of course, hydrolyzed and, in that form, are eventually separated from the desired product as, e.g., sodium hydroxide or ethyl alcohol. Defining R is exceedingly difficult since it is hard to conceive of a radical which, if hydrolyzable, could not be used here. An arbitrary limitation has been therefor selected to avoid problems which might exist in various complex and exotic molecules. The simplest R radicals included are straight or branched chain substituted or unsubstituted alkyl radicals having 1 to 10 carbon atoms, e.g., methyl, ethyl, and isopropyl. On the inorganic side, elements of Group 1a of the Periodic Table, e.g., sodium, potassium, or lithium, are representative. Other examples of R radicals are acetyl, $CH_3CO$—, and phenyl, $C_6H_5$—.

$R^1$ is defined as an unsubstituted or substituted straight or branched chain divalent saturated alkylene radical having 1 to 10 carbon atoms or an unsubstituted or substituted divalent aryl radical having 1 to 3 benzene rings wherein the substituents for the alkylene radical can be halogen or a phenyl radical and the substituents for the aryl radical can be halogen or straight or branched chain saturated alkyl radicals having 1 to 5 carbon atoms. In its broadest sense, the $R^1$ radical should be one that does not contain any functional group which would interfere or react with the phosphorus atom in the formula as, e.g., a carboxyl radical would do. Examples of $R^1$ radicals are —$(CH_2)_2$—, —$(CH_2)_3$—, —$(CH_2)_5$—, phenylene, i.e.,

diphenylene, i.e.,

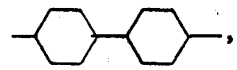

1,6 dinaphthyl

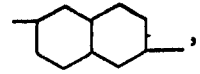

and 1,6 dianthralene

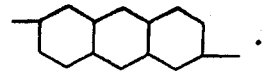

A substituent for the alkylene or aryl radicals can also be —$P(R^2)_2$ wherein $R^2$ is as defined herein. Unsubstituted straight chain alkylene radicals having 2 to 5 methylene groups are preferred.

$R^2$ is similar in definition to $R^1$ except that it is monovalent. It can be defined as an unsubstituted or substituted straight or branched chain or cyclic monovalent saturated alkyl radical having 1 to 10 carbon atoms or an unsubstituted or substituted monovalent aryl radical having 1 to 3 benzene rings wherein the substituents for the alkyl radical can be halogen or a phenyl radical and the substituents for the aryl radical can be halogen or straight or branched chain saturated alkyl radicals having 1 to 5 carbon atoms. Again, in the broadest sense the $R^2$ radical should be one that does not contain any functional groups which would interfere or react with the phosphorus atom in the formula, e.g., carboxyl.

While the phenyl radical is preferred here, other examples of R radicals are methyl, ethyl, benzyl, or cyclohexyl.

It should be noted that the limited definitions of R, $R^1$ and $R^2$ mentioned heretofore are arbitrary and merely selected in order to reduce the complexity of the precursors and catalyst. Theoretically, there is no reason why the number of atoms or benzene rings cannot be doubled or tripled with similar results.

The number of recurring units or molecular weight of the second precursor is, in view of its nonlinearity, difficult to ascertain. Generally, the number of units will range from about 3 to 1000 and the the molecular weight from about 750 to about 300,000. The objective, however, is to provide a solid polymeric catalyst composition which is insoluble in the reaction medium in which it will be used. Higher molecular weights where desired can be provided by heating the hydrolyzed products at temperatures of between 100° C. and 300° C. for longer periods of time. In the same vein mixed compositions of one or more polymers of varying size and complexity can be used to provide the catalyst or for recovery of spent metal.

The polymer of this invention is a non-linear or branched homopolymer, the most commonly occurring bond being between Si and O. As noted, sufficient R radicals may remain on hydrolysis to end-block or terminate the polymer. Mixtures of first precursors can be used to prepare the second precursor, if desired, although this is not preferred. As noted, cross linking agents such as tetrafunctional silicate esters can be cohydrolyzed with the first precursor. The resulting copolymer will contain cross-link units represented by the following structural formula:

$$R^3O\ Si - O_{3/2}$$

wherein $R^3$ is defined in the same manner as $R^2$. The cross-link units can be present in amounts of about 1 to about 20 mol percent. This is simply derived by cohydrolyzing cross-linking agents in an amount of about 1 to 20 mol percent based on the number of mols of first precursor hydrolyzed. The use of the cross-linking agent eliminates the stickiness of low molecular weight polymers, and reduces the number of phosphorus atoms in the final polymer where lesser amounts of complexing are desired. A preferred amount of cross-linking agent is about 5 to about 15 mol percent. End-blocking is theoretically the same as for the second precursor. Examples of cross-linking agents are tetraethyl orthosilicate, tetraphenyl orthosilicate, silicon tetrachloride, and methyl trichlorosilane. The cross-link units are randomly interspaced among the units of the polymer.

The catalyst composition consists essentially of the second precursor (which may be cross-linked as described) wherein each phosphorus atom in the polymer is coordinated with a transition metal atom having a zero or positive charge, each positively charged transition metal atom having a sufficient number of negatively charged organic or inorganic radicals, devoid of functional groups, attached thereto to satisfy the valence of said transition metal atom, and wherein the radicals are selected from the group consisting of halogens; nitrates; sulfates; straight chain alkoxy or acyloxy radicals having 1 to 10 carbon atoms; and aryloxy radicals having 1 to 3 benzene rings. Since each transition metal atom has one to six coordination sites and a phosphorus atom has one coordination site, a transition metal may satisfy from one to six of the polymer's recurring units. The transition metal can be any one of the transition elements mentioned in the Periodic Table, or can be two or more different transition metals. Generally, a metal is selected according to the process in which the catalyst is to be used. Platinum, palladium, and platinum/palladium are preferred. Examples of other transition metals are vanadium, chromium, cobalt, nickel, rhodium, and tungsten. As long as functional groups are avoided, a wide range of transition metal compounds can be used. Generally, the inorganic metallic compound or the organo-metallic compound used in the complexing process is withdrawn from a solution by the second precursor and becomes a part of the catalyst composition or complex by coordination of the phosphorus atom with the transition metal atom. The radicals which, with the transition metal, make up the transition metal compound are mentioned above. Examples of these radicals are Cl, Br, $NO_3$, acetate, propionate, butyrate, and sulfate. An example of both alkoxy and acyl is the important acetylacetonate radical.

The use of the catalyst compositions of this invention in appropriate processes is advantageous in that the problem of recovery and recycle of precious metals prevalent in homogeneous catalysis is substantially eliminated, continuous process reactions are facilitated by passing the reactants through a fixed bed of the catalyst composition; catalyst removal from products is obviated; heat removal and therefore reaction control is simplified; catalyst economics are improved; a particular product can be produced at lower cost; and turnover, the number of pounds of product secured by the use of one pound of catalyst (the metal itself) is increased.

As noted above, the second precursor, i.e., the polymer per se, finds utility, other than in the preparation of the catalyst composition, in the recovery of precious metals after their use in homogeneous catalysis. The second precursor is used in the manner of an ion-exchange body, the catalyst metal-bearing fluid from a homogeneous catalytic process flowing through the second precursor and complexing with it. Regeneration of the second precursor and metal recovery can then be accomplished by conventional processes such as displacement, heating, or even ashing and leaching with acids.

The second precursor can be considered a silicate back-bone carrier polymer and, as noted, the formula for the recurring unit can be written as follows:

$$-O_{3/2}Si-R^1-P(R^2)_2$$

wherein the numerator 3 designates the residual functionality of Si, i.e., the number of oxygen atoms; and the denominator 2 designates that each oxygen is shared, generally, with another Si atom.

The catalyst composition is useful in the hydroformylation of olefins, including the OXO process; hydrogenation of olefins, dienes, and acelylenes; isomerization of olefins, polymerization of dienes, or acetylenes; acetoxylation of olefins; silylation of olefins; addition reactions of the double bond; oligomerization — addition to the double bond in dienes; addition — elimination reactions; and hydrocyanation of olefins.

The following reaction schemes illustrate the complexity of the reactions which take place in the preparation of the first and second precursors. The heading recites the ultimate silisesquioxane, the second precursor. The subscript n designates the number of theoretical recurring units. End-blocking radicals are not shown.
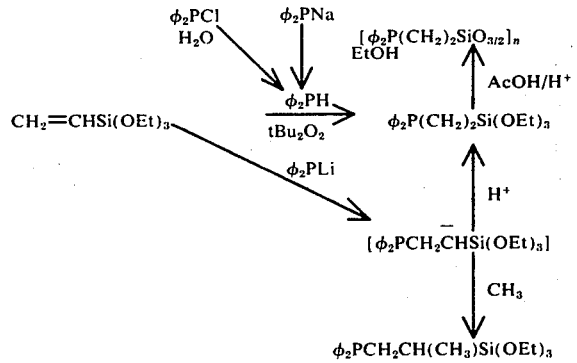
SCHEME I
2(DIPHENYLPHOSPHINYL)ETHYL SILSESQUIOXANE
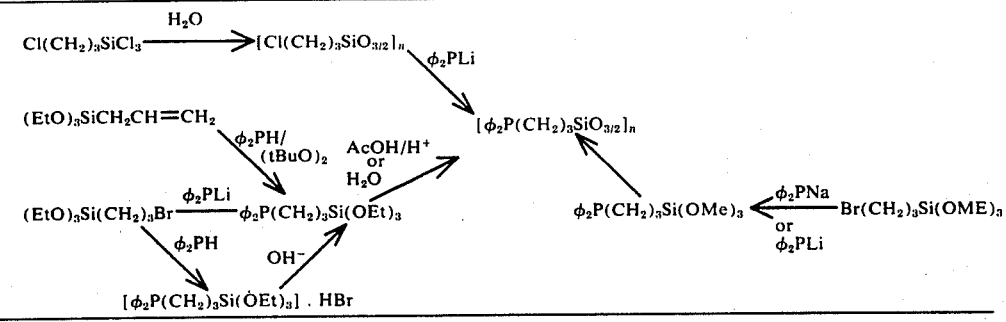
SCHEME II
3(DIPHENYLPHOSPHINYL)PROPYL SILSESQUIOXANE
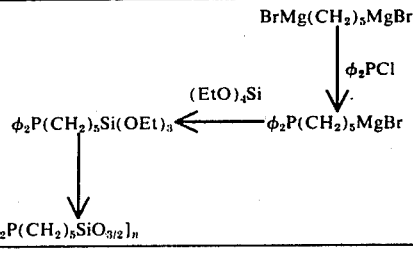
SCHEME III
5(DIPHENYLPHOSPHINYL)PENTYL SILSESQUIOXANE

SCHEME IV p-(DIPHENYLPHOSPHINYL)PHENYL SILSESQUIOXANE,
p-(DIPHENYLPHOSPHINYL)BIPHENYL-p'-SILSESQUIOXANE

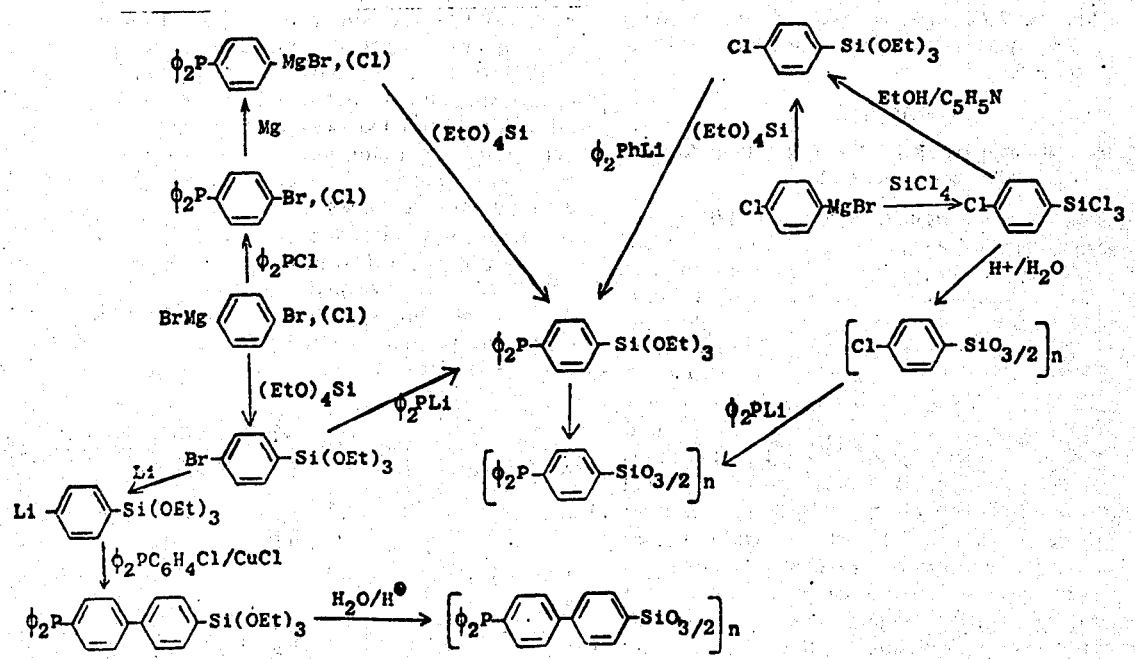

The following examples illustrate the invention and include the preparation of known precursors and processes using the ultimate catalyst composition. Conventional analytical techniques are followed.

EXAMPLE 1

Diphenylphosphine

A. By Hydrolysis of Diphenylphophinous Chloride. Diphenylphosphinous chloride (700 g, 3.17 mols) is added with rapid stirring to 1400 ml of distilled water. The temperature rises to 70° C. The solution is heated at reflux 1 hour, then cooled. The lower organic layer is separated from the water, dried, and distilled in vacuum giving diphenylphosphine (207 g, 70 percent yield), b.p. 151° C/10 mm. From the residue, 327 g (95 percent yield) of diphenylphosphonic acid is obtained by recrystallization from ethanol.

B. From Sodium Diphenylphosphide. To a suspension of sodium "sand" (4.6 g, 0.2 g atom) in a 100 ml of anhydrous dioxane heated at 65°–70° C. under nitrogen, a solution of diphenyl phosphorus chloride (22 g., 0.1 ml) in 50 ml of anhydrous dioxane is added during 1 hour. The solution is heated at reflux temperature (100° C) for 4 hours until all of the sodium is consumed. Then, after cooling to 10° C. 30 ml anhydrous ethanol is dropped in, followed by 25 ml of water to dissolve the sodium chloride. The organic layer is separated and the water is extracted with ether. The organic layers are dried and distilled in vacuum giving diphenylphosphine (14.14 g, 76 percent yield).

EXAMPLE 2

2-(Diphenylphosphinyl) ethyl Triethoxysilane.

To diphenylphosphine (18.6 g, 1.0 mol) heated to 140° C. under nitrogen, a mixture of vinyl triethoxysilane (19.0 g, 1.0 mol) and di-t-butyl peroxide (1.92 g) is added with stirring during ¾ hour. The solution is held at 140°–160° C for an additional hour. Distillation in vacuum gives the product (24.7 g, 65.7 percent yield, b.p. 162° C/0.3 mm, $n_D^{27}$ 1.5370. The efficiency on the basis of the vinyl silane consumed is 93 percent. The H'NMR, delta ($C_6H_6$): 0.8 (m, 2H). 1.12 (t, 9H); 2.24 (m, 2H); 3.76 (q, 6H); and 7.0–7.7 (m, 10H) is consistent with the expected structure.

EXAMPLE 3

Poly-2-(Diphenylphosphinyl)ethyl Silsesquioxane.

A. 2-(Diphenylphosphinyl)ethyl triethoxysilane (37.6 g, 0.1 mol) dissolved in 100 ml of acetic acid containing 10 drops of concentrated hydrochloric acid is heated 2 hours at reflux temperature. The solvents are removed by distillation and 200 mesh silica gel (26.5 g) is added to the residue. The mixture is dried at 300° C under nitrogen for 4 hours then, after cooling, powdered. The yield is 47 grams, 88.7 percent of theory. It analyzes 1.48 meq. P/gram. Calcd. for $C_{14}H_{14}PSiO_{3/2}$·$SiO_2$ P = 5.85 percent. Found: P = 4.59 percent.

B. 2-(Diphenylphosphinyl)ethyl triethoxysilane (37.6 g, 0.1 mol) and tetraethylorthosilicate (2.08 g, 0.01 mol) are cohydrolyzed in an identical manner. There is recovered 26 grams of solid analyzing 11.04 percent P (3.56 meq. P/gram). The infrared spectrum shows absorption bands consistent with the functional groups of the expected structure. The H'NMR spectrum shows broad resonance peaks at delta (acetone $d_6$): 0.7 (2H, Si—CH$_2$—); 2.1 (2H, Si—C—CH$_2$—); 6.3 (10H).

EXAMPLE 4

1,2-Dibromoethyl Triethoxysilane.

To vinyl triethoxysilane (19.0 g, 0.1 mol) dissolved in 150 ml carbon tetrachloride containing 0.5 g NaBr and cooled to 0° C, 16 g (0.1 mol) of bromine dissolved in 150 ml of carbon tetrachloride is added in the dark over a period of 7 hours, allowing the bromine color to be substantially discharged after each addition. The material is distilled in vacuum giving 32 grams (91.4 percent yield) of product; b.p. 88° C/1 mm; $n_D^{27}$ 1.4620. The H'NMR delta (CD Cl$_3$): 1.24 ($t$, 9H); 3.19–4.15 ($m$, 3H); 3.9 ($q$,6H) is consistent with the expected structure.

EXAMPLE 5

2-(Diphenylphosphinyl) ethyl Triethoxysilane Anion. Neutralized with H$^+$.

To a suspension of sodium diphenylphosphide prepared, under nitrogen in dry toluene (100 ml), from sodium (4.6, 0.2 g atom) and diphenylphosphinous chloride (22.0 g, 0.1 mol), vinyl triethoxysilane (19.0 g, 0.1 mol) is added during 45 minutes. A slight temperature rise occurs. The temperature is held at 30° C by adjusting the feed rate of the vinyl silane. After 3 hours, 5 ml anhydrous ethanol is added. The yellow color of the anion is instantly discharged. The solution is filtered to remove inorganic salts. Gas chromatographic analysis confirms the presence of diphenyl phosphine and 2-(dipenylphosphinyl)ethyl triethoxysilane. After neutralization with carbon dioxide, the liquid is distilled giving 6.3 g (16.7 percent yield) of 2-(diphenylphosphinyl) ethyl triethoxysilane and 3.0 g (16.3 percent yield) of diphenylphosphine. The H'NMR spectrum of the silane is identical to that of the product of addition of diphenylphosphine to vinyl triethoxysilane with a radical initiator.

EXAMPLE 6

Reaction with Methyl Iodide

A diphenylphosphide anion suspension prepared under nitrogen from sodium (4.6 g, 0.2 g atom) and diphenylphosphinous chloride (22.0 g, 1 mol) in 100 ml of dry toluene is added to vinyl triethoxysilane (19.0 g, 0.1 mol) at 30° C. After stirring for a short period methyl iodide (14.19 g, 0.1 mol) is slowly added. The temperature rises rapidly to 40° C. and is reduced to 25° by cooling with ice water. The addition is completed in ½ hour during which the bright yellow solution turns to a light gray color. The precipitated inorganic salt is filtered off under nitrogen in a drybox, and the toluene concentrated in vacuum, to give 25 g of a light yellow liquid. The material distilled in vacuum gives 1-(diphenylphosphinyl)propyl-2-triethoxysilane, b.p. 148°–150° C/0.1 mm. The H'NMR delta(C$_6$D$_6$): 0.6 ($d$, 3H); ~0.8 (m, H); 1.14 ($t$, 9H); 2.24 ($m$, 2H); 3.75 ($q$, 6H); 6.9–7.6 (m, 10H) is consistent with the structure.

EXAMPLE 7

Allyl Diphenylphosphine.

A solution of the Grignard reagent in 250 ml of diethyl ether is prepared using 12.2 grams (0.5 g atom) of magnesium turnings and 60.5 grams (0.5 mol) of redistilled allyl bromide. The solution is forced by nitrogen pressure through glass tubing terminating in a fine glass filter-frit into a 500-ml feed funnel. Analysis of the solution shows a content of 0.4 mol (80 percent) of allyl magnesium bromide. This solution was added over a period of 3½ hours to a solution of 75 g (0.34 mol) of diphenylphosphinous chloride in 140 ml of anhydrous diethyl ether in a nitrogen atmosphere. The reaction is completed by refluxing the mixture for an additional 2 hours. It is then cooled to 5° C. and poured, still under nitrogen, into a mixture of ice and 20 percent ammonium chloride solution. The isolation of the product is done in an atmosphere of nitrogen, avoiding exposure to the air as much as possible. The ether layer is extracted three times, each with 25 ml of ether. The ether layers are combined, washed with water, dried over anhydrous magnesium sulfate, and finally distilled. The material boiling at 117° C. at 0.1 mm is collected (61.5 g, 80 percent yield), leaving a residue of 7 grams. The residue is recrystallized from chloroform, m.p. 195° C. The residue is largely diphenylphosphonic acid, apparently from the hydrolytic dismutation of unreacted diphenylphosphinous chloride. The H'NMR spectrum of the distilled liquid: delta (C$_6$D$_6$): 2.75 ($d$, 2H, J = 8 cps) assigned to

Ⓑ;

4.9 ($d—d$, 2H, J = 14, 3 cps) assigned to

Ⓓ;

5.75 ($m$, H)

Ⓒ;

7.2 ($m$, 10H)

Ⓐ confirms the structure, (C$_6$H$_5$)$_2$PCH$_2$CH=CH

An impurity giving a complicated resonance near delta, 7.4, probably due to diphenylphosphonic acid in small amount, is also present.

EXAMPLE 8

Reaction of Diphenylphosphine with 3-Bromopropyl Triethoxysilane.

A solution of diphenyl phosphine (18.6 g, 0.1 mol) and 3-bromopropyl trimethylsilane (28.5 g, 0.1 mol) in 100 ml of dry toluene is heated at reflux for one hour. After cooling the solution, 10 percent sodium hydroxide (0.1 mol) is added. The toluene layer is separated, washed with water and dried. The clear liquid separates on standing into two layers, the lower one finally crystallizing. The solid (0.746 g) is filtered off. It melts above 300° C. and is probably the hydrobromide product. The filtrate is distilled in vacuum giving 31 grams (79.5 percent) of 3-(diphenylphosphinyl)-propyl triethoxysilane, having boiling point, refractive index, and retention time on gas-liquid chromatography, identical with the material prepared from lithium diphenyl phosphide.

EXAMPLE 9

3-(Diphenylphosphinyl)propyl Triethoxysilane

To diphenylphosphine (18.0 g, 0.097 mol) heated to 140° C under a nitrogen atmosphere, a mixture of allyl triethoxysilane (19.8 g, 0.97 mol) and di-t-butyl peroxide (1.86 g) is added during ¾ hour. Heating is continued for 1 hour after the addition is complete. Analysis of the liquid shows the presence of unreacted phosphine and allyl silane, so di-t-butyl peroxide (2.0 g) is added and heating continued 2 hours more. This analysis, addition, and heating is repeated once more, after which only a trace of diphenylphosphine is present. The liquid reaction mixture is distilled giving the product (11.2 g, 30 percent yield), b.p. 180–184° C/0.7 mm, $n_D^{27}$ 1.5340.

EXAMPLE 10

3-(Diphenylphosphinyl)propyl Triethoxysilane

To lithium shavings (2.76 grams, 0.4 g atom) in 200 ml of dry tetrahydrofuran, redistilled diphenylphosphinous chloride (44 grams, 0.2 mol) dissolved in 100 ml of tetrahydrofuran is added during one hour while stirring rapidly at room temperature, in a dry nitrogen atmosphere. The lithium metal dissolves giving a blood-red solution of lithium diphenylphosphide. To this solution 50.8 grams (0.18 mol). of 3-bromopropyl triethoxysilane is added during 1 hour at 22°–25° C. At the end of the addition the solution changes to a pale yellow color. Analysis of this solution by gas-liquid chromatography (10 feet × ¼ inch SE-30 on Chromosorb W at 200° C) shows 1.8 percent unreacted silane and 97.35 percent 3-(triethoxysilyl)propyl diphenylphosphine. The tetrahydrofuran is distilled off in vacuum and benzene added to precipitate lithium chloride, which is filtered off. The filtrate is distilled in vacuum to give 44.6 grams (63.3 percent yield) of product, b.p. 115°–157° C/0.2 mm; $n_D^{22.5}$ 1.5358. The H'NMR, delta ($C_6D_6$): 1.13 ($t$, 9H); 4.22 ($q$, 6H); 0.85 ($t$, 2H); 1.3–2.0 ($p$, 2H); 2.02 ($t$, 2H); 7.0–7.7 ($m$,10H) is consistent with the expected structure. From a similar experiment on a larger scale (0.5 mol), a yield of 76 percent is obtained.

In a similar manner, 3-chloropropyl triethoxysilane is used in the reaction with lithium diphenylphosphide to give the product in yield of 62.2 percent (58.1 percent distilled) and efficiency of 100 percent based on the silane used.

EXAMPLE 11

Reaction of 3-Bromopropyl Trimethoxysilane with Lithium Diphenylphosphide.

Diphenylphosphinous chloride (22 g, 0.1 mol) is added slowly (1⅔ hours) to a suspension of lithium metal (1.38 g, 0.2 g atom) in 100 ml of dry tetrahydrofuran at 15°–20° C while maintaining a nitrogen atmosphere over the liquid. To the blood-red solution, 3-bromopropyl trimethoxysilane (24.3 g, 0.1 mol) dissolved in 50 ml of dry tetrahydrofuran is added over 1 hour at 22°–25° C. The color changes to light yellow near completion of the addition of the silane. Precipitated lithium salts are filtered off under a dry nitrogen atmosphere. Gas-liquid chromatography (200° C, 10 feet × ¼ inch 10 percent SE-30 on Chromosorb W column, 50 ml/min helium) shows two major peaks at a retention time of 1.6 minutes, identified as the unreacted bromosilane, and the other at 18 minutes. The solvent is removed in vacuum and the bromosilane is recovered by distillation at reduced pressure, leaving a glassy residue insoluble in acetone, chloroform, benzene, ether, water, and tetrahydrofuran, and not melting below 300° C. The infrared spectrum of the solid shows strong bands at 2.93 and 6.15 microns due to water and bands at 3.4, 3.28, 6.3, 6.75, 6.96, 8.47, 9.0, 9.4, 13.45, 13.93, and 14.47 microns, but no methyl band at 12.3 microns.

The H'NMR spectrum (hot $C_2D_5OD$) confirms the absence of the methyl group and the presence of the polymeric structure, $[(C_6H_5)_2P(CH_2)_3—SiO_{3/2}]n$.

EXAMPLE 12

Allyl Diphenylphosphine Oxide

A mixture of diphenylphosphine chloride (11 g, 0.05 mol), allyl alcohol (2.9 g, 0.05 mol) in 50 ml of anhydrous ether is stirred at room temperature while slowly adding pyridine (4.0 g, 0.05 mol) to it. After 40 minutes, the pyridine hydrochloride is filtered off and the ether removed by distillation. The liquid residue is heated to 150°, whereupon an exothermic reactions sets in raising the temperature quickly to 178° C. The material is then distilled, b.p. 168°–175° C/0.4 mm, whereupon it crystallizes, m.p. 108° identical to the allyl diphenylphosphine oxide made by oxidation of the phosphine. Allyl diphenylphosphine oxide prepared by this method is reported; b.p. 200°–202° C/2 mm; m.p. 94°–96° C.

EXAMPLE 13

Reduction of Diphenylphosphine Oxide by Trichlorosilane.

Allyl diphenylphosphine oxide (11.8 g, 0.05 mol) in 50 ml of dry benzene is stirred under a nitrogen atmosphere while slowly adding trichlorosilane (13.5 g, 0.1 mol). During the addition the temperature increases to 45° C. The solution is heated at reflux temperature for 2 hours, then cooled and neutralized with 40 percent aqueous sodium hydroxide solution. The benzene layer is washed until neutral, dried over sodium sulfate, and distilled; b.p. 128°–135° C/0.2 mm, yield 9.1 g, 81 percent of theory. The H'NMR spectrum is consistent with the allyl diphenylphosphine structure and with material prepared from allyl magnesium bromide.

EXAMPLE 14

Poly-(3-diphenylphosphinyl)propyl Silsesquioxane (3-Diphenylphosphinyl)propyl triethoxysilane (39 g, 0.1 mol) dissoleved in 100 ml of acetic acid containing 10 drops of concentrated aqueous HCl is refluxed for 2 hours. The ethyl acetate and acetic acid are distilled off and the residue evaporated to dryness on a hot plate. The glassy solid is pulverized and mixed with 30 grams of 38–200 mesh silica gel and repulverized. It is heated overnight in an oven at 200° C. The white solid has a phosphorous content of 4.47 percent, equivalent to 1.44 meq. P/gram. The recovery is 86.5 percent of theoretical. The infrared spectrum shows absorption bands at 3.26 microns (aromatic CH); 6.31, 6.75, 6.97 microns (aromatic double bond); 13.6, 14.5 microns (mono substituted phenyl); 3.42, 7.8 (methyl-ene) and a strong broad absorption from 9 to 11 microns characteristic of the Si—O group A second preparation as above, but with the addition of 2.08 grams (0.01 mol) of tetraethyl orthosilicate as a cross-linking agent, gives a solid having an active material content of 3.5 meq./gram. Analysis: Found: P = 10.50; Calculated 10.87 percent. The infrared spectrum shows absorption bands identical with the first material.

EXAMPLE 15

Hydrolysis of 3-(Diphenylphosphinyl)propyl Triethoxysilane

The compound (5.0 g, 0.0128 mol) is refluxed 4 hours in 25 ml of distilled water. The water is evaporated and the residue dried at 300° C. in an oven under nitrogen. A glassy solid (2.5 g) is recovered. The material has an infrared spectrum identical to the product of the trans-esterification reaction, and an H'NMR spectrum, delta(acetone-$d_6$): 0.55 ($m$, 2H), 1.42 ($m$, 2H), 1.95 ($m$, 2H), 7.0–8.0 ($m$, 10H), consistent with poly(3-diphenylphosphinyl)propyl silsesquioxane [$O_2P(CH_2)_3Si)_{3/2}]_n$. It is soluble in acetone, dimethylformamide, dimethylsulfoxide, but insoluble in water, ethanol and methanol.

EXAMPLE 16

3-(Diphenylphosphinyl)propyl Trimethoxysilane

Sodium metal (4.6 g, 0.2 g atom) is dispersed in 100 ml of dry toluene, heated to 65°–70° C. and diphenylphosphinous chloride (22 g, 0.1 mol) added with vigorous stirring over 3½ hours, while maintaining an atmosphere of dry nitrogen above the liquid. After stirring overnight the sodium is consumed and a deep yellow suspension of $(C_6H_5)_2PNa$ and sodium chloride is obtained. To this, 3-bromopopyl trimethoxysilane (24.3 g, 0.1 mol) is added during one hour. A gentle heat evolution occurs and the liquid is maintained at 40° C. by cooling. After the addition is completed, the reaction mixture is heated to reflux temperature for 30 minutes. The color changes to a light gray. The solution is cooled, filtered to remove salts, and concentrated in vacuum. The residue is distilled giving 23 grams (66 percent) of product; b.p. 174° C/0.08 mm. The H'NMR spectrum, delta($C_6D_6$): 0.83 ($m$,2H); 1.60 ($m$, 2H); 2.00 ($m$, 2H); 3.40 (S, 9H), and 6.98–7.65 (m, 10H) is consistent with the structure of the expected product.

EXAMPLE 17

5-(Diphenylphosphinyl)pentyl Triethoxysilane

To the solution under an atmosphere of nitrogen of di-Grignard reagent prepared from magnesium (9.7 g, 0.4 g atom) and 1,5-dibromopentane (46.0 g, 0.2 mols) in 600 ml anhydrous ether, that analyzed 0.172 equivalent (43 percent) content, diphenylphosphinous chloride (22.0 g, 0.1 mol) dissolved in 100 ml of tetrahydrofuran is added under nitrogen at 15° C with stirring during 2 hours. The solution is then refluxed ½ hour. The solution is cooled and forced by nitrogen pressure through a fine-glass, filterstick into a feed funnel. Analysis shows a Grignard content of 0.0952 equivalents. This solution is added during 1½ hours under nitrogen with stirring to a solution of redistilled tertaethyl orthosilicate (83 g, 0.4 mol) in 100 ml of tetrahydrofuran. The solution is then heated at reflux for 2 hours. The liquid then washed with a solution of ammonium chloride (30 g) in ice water. The organic layer is separated, washed twice with water, dried, and then concentrated in vacuum. A small amount of solid is removed by filtration and the liquid is fractionated in vacuum under nitrogen. After distillation of excess ethyl silicate, the remainder (12.7 g) boiled in the range 165°–210° C/0.2 mm. By gas-liquid chromatography, it is shown to contain three compounds with retention times of 11.8, 15.8 and 42.5 minutes, the first and third being major components. Each of these is collected and its H'NMR spectrum determined. The less volatile delta ($CCl_4$): 1.15 ($t$, 3H); 3.70 ($q$, 2H) is identified as a low polymer of ethyl silicate. The more volatile delta ($C_6D_6$): 0.72 ($d$–$d$, 2H); 0.4–1.7 ($m$,6H) 1.15 ($t$, 9H); 1.90 (split 7, 2H); 3.72 ($q$, 6H); 6.8–7.7 ($m$, 10H) confirms the structure as 5-(diphenylphosphinyl) pentyl triethoxysilane.

EXAMPLE 18

4-Chlorophenyl Diphenylphosphine

The Grignard reagent is prepared from 1-bromo-4-chlorobenzene (191 g, 1.0 mol) and magnesium (24.34 g, 1 g atom) in 600 ml dry ethyl ether in the usual way, but holding the temperature below +2° C to avoid formation of a dimagnesium compound. To this solution, diphenylphosphinous chloride (220.5 g, 1.0 mol) in 100 ml of dry ether is added below 10° C during 1½ hours. The solution is refluxed for ½ hour. The precipitated salts are dissolved by adding 100 ml saturated ammonium chloride solution. The ether is separated, dried, and distilled, giving 248 grams (83 percent yield) of the product homogeneous by gas-liquid chromatography: b.p. 157° C/0.08 mm; $n_D^{25}$ 1.6608. Its H'NMR spectrum is characteristic of aromatic protons only. The infrared spectrum, at 3.26, 5.12, 5.27, 5.30, 5.52, 5.69, 6.31, 6.35, 6.75, 6.97, 9.2, 9.75, 9.88, 12.25, 13.57, 14.43 microns, confirms the 4-chlorophenyl diphenylphosphine structure. Calculated for $C_{18}H_{14}PCl$: C = 72.86 percent, H = 4.76 percent, P = 10.44 percent, Cl = 11.95 percent. Found: C = 72.83 percent, H = 4.85 percent, P = 10.17 percent, Cl = 11.69 percent.

EXAMPLE 19

4-Bromophenyl Diphenylphosphine

To a monoGrignard reagent solution prepared in 79 percent yield (by titration) from p-dibromobenzene (236 g, 1.0 mol) and magnesium (27.5 g, 1.15 g atom) in 1150 ml of dry diethyl ether, diphenylphosphinous chloride (173.8 g, 0.79 mol) in 100 ml of ethyl ether is added over 1½ hours at −20° C to 0° C. After the addition, the reaction is heated to reflux temperature. The precipitated salts are dissolved with 350 ml saturated aqueous ammonium chloride solution and ice. The ether layer is separated, washed, dried, and distilled, giving 193.5 grams (71.8 percent yield based on the Grignard reagent) of 4-bromophenyl diphenylphosphine, b.p. 188°/0.10 mm and m.p. 71°–73° C.

EXAMPLE 20

4-(Triethoxysilyl)phenyl Diphenylphosphine

To a Grignard reagent solution prepared from 4-bromophenyl diphenylphosphine (36 g, 0.1 mol) and magnesium (2.43 g, 0.10 g atom) in 130 ml of dry tetrahydrofuran, tetraethyl orthosilicate (54 g, 0.21 mol) is added and the solution heated at 55° C for 4 hours. The solvent is removed in vacuum leaving 27 grams of clear liquid, analyzing 50 percent product by gas-liquid chromatography. A sample separated by this means gave a H'NMR, delta ($C_6D_6$): 8.84 ($t$, 9H); 3.74 ($q$, 6H); 6.90–7.90 ($m$, 14H), consistent with the structure expected. The yield is 32 percent.

EXAMPLE 21

4-Bromophenyl Triethoxysilane

To a filtered mono-Grignard reagent solution prepared in 78.2 percent yield from p-dibromobenzene (236 g, 1 mol) and magnesium (27.5 g, 1.15 g atom) in 1175 ml of dry ether, tetraethyl orthosilicate (487 G, 2.34 mols) in 400 ml of dry ether is added in 15 minutes while maintaining a blanket of nitrogen above the liquid. The temperature rises from 24° to 37° C. It is then refluxed one hour. The reflux condenser is replaced with one arranged for downward distillation and the ether is removed while replacing it by adding dry toluene (800 ml) to the reaction mixture. Magnesium salts are precipitated by this operation. These are filtered off under an atmosphere of nitrogen. The filtrate is stripped of toluene and the residue distilled in vacuum giving 161.5 g (64.6 percent yield based on the Grignard reagent) of 4-bromophenyl triethoxysilane, b.p. 90° C/0.3 mm, 115° C/1.9 mm, $n_D^{25}$ 1.4872. The H'NMR, delta $(C_6D_6)$: 1.18 (t, 9H); 3.82 (q, 6H); 7.50 (m, 4H) is characteristics of the structure expected.

EXAMPLE 22

4-(Diphenylphosphinyl)phenyl Triethoxysilane

To the lithium diphenylphosphide solution prepared under nitrogen from lithium (0.6246 g, 0.09 g atom) and diphenylphosphinous chloride (9.92 g, 0.045 mol) in 50 ml dry tetrahydrofuran, 14.5 g (0.045 mol) of 4-bromophenyl triethoxysilane dissolved in 50 ml dry tetrahydrofuran is added during one hour. The blood-red solution turns to a light brown color with the appearance of a small amount of white solid. The solution is filtered under nitrogen, diluted with benzene to precipitate remaining lithium bromide, and refiltered. Analysis of the solution by gasliquid chromatography shows a content of unreacted bromosilane of 3.88 grams (0.0122 mol). Distillation in vacuum gives 4-(diphenylphosphinyl)phenyl triethoxysilane (13 grams, 68.1 percent yield), b.p. 164°–167° C/0.1 mm. The H'NMR spectrum is identical to the material prepared from 4-(diphenylphosphinyl)phenyl magnesium bromide and tetraethyl orthosilicate. The efficiency based upon bromosilane consumed is 93.4 percent.

EXAMPLE 23

Using 4-Chloro Compound

To a suspension of lithium (2.1 g, 0.3 g atom) in 150 ml of anhydrous tetrahydrofuran held under nitrogen, a solution of triphenylphosphine (26.2 g, 0.1 ml) in 150 ml dry tetrahydrofuran is added in a period of ½ hour. The temperature rises from 25° C to 55° C. The solution turns blood-red and nearly all of the lithium dissolves in 3 hours. To this solution t-butyl chloride (9.3 g, 0.1 mol) is added to destroy the phenyl lithium. The solution is filtered, and to it 4-chlorophenyl triethoxysilane (27.5 g, 0.1 mol) dissolved in 50 ml of dry tetrahydrofuran is added and the solution refluxed 4 hours. The red color is not fully discharged in this time due to the sluggish nature of the nucleophilic displacement of the aryl chloride. The excess lithium diphenylphosphide is destroyed by addition of 25 ml of ethanol and finally, water. The solvents are removed in vacuum. The liquid is taken up in toluene and filtered to remove precipitated lithium chloride. Gas-liquid chromatographic analysis of this solution shows the presence of recovered chlorophenyl silane, triphenylphosphine, and only a small amount (estimated 15 percent yield) of 4-(diphenylphosphinyl)phenyl triethoxysilane.

EXAMPLE 24

4-Chlorophenyl Trichlorosilane

The Grignard reagent solution prepared, under nitrogen, from 1-bromo-4-chlorobenzene (38.3 g, 0.2 mol) and magnesium (4.867 g, 0.2 g atom) in 300 ml anhydrous diethyl ether, is filtered through a glass filterstick by nitrogen pressure into a graduated feed-funnel, from which it is fed during 2¼ hours into a stirred solution of redistilled silicon tetrachloride (102 g, 0.6 mol) in 200 ml of dry ether. The solution is heated at reflux temperature an additional 2 hours, then cooled and filtered under nitrogen. If not protected from the air, the solution turns red and reduced yields are obtained. The ether and excess silicon chloride is concentrated in vacuum and the residue distilled in vacuum under nitrogen. 4-Chlorophenyl trichlorosilane (17 g, 35 percent yield), b.p. 84°–85° C/3.4 mm, $n_D^{27.5}$ 1.5400, and bis(4-chlorophenyl) dichlorosilane (6.2 g, 20 percent yield), b.p. 146°–150° C/0.4 mm, m.p. 60°–61° C are obtained.

EXAMPLE 25

4-Chlorophenyl Trimethoxysilane

To a solution of 4-chlorophenyl trichlorosilane (49.1 g, 0.2 mol) in anhydrous methanol (27.6 g, 0.86 mol) heated to 65° C, a solution of anhydrous pyridine (47.5 g, 0.6 mol) in 150 grams of dry benzene is added, keeping the temperature at 65° C after the addition is complete. The pyridine hydochloride is removed by filtration and the filtrate is distilled in vacuum, giving 4-chlorophenyl trimethoxysilane (33.4 g, 72 percent yield), H'NMR, delta $(CCl_4)$: 3.56 (s, 9H); 7.41 (m, 4H), consistent with the expected structure.

EXAMPLE 26

4-Chlorophenyl Triethoxysilane from (i) 4-Chlorophenyl Trichlorosilane.

This is prepared by the same method as the corresponding methoxysilane, but using anhydrous ethanol (27.6 g, 0.6 mol) in place of methanol. Distillation gives the product (55 g, 100 percent yield), b.p. 150°–107° C/2 mm, $n_D^{25.5}$ 1.4740, H'NMR, delta $(C_6D_6)$: 0.83 (t,9H); 3.89 (q, bH); 7.55 (m, 4H), and from (ii) 4-Chlorophenyl Magnesium Bromide. The Grignard reagent solution prepared to 63 percent yield from 1-chloro-4-bromobenzene (114.9 g, 0.6 mol) is added to a solution of redistilled tetraethyl orthosilicate (249.6 g, 1.2 mol) in 300 ml anhydrous ether at 0°–10° C during 2½ hours. After completion of the feed, the mixture is heated at reflux temperature for 2 hours, then cooled, and filtered under a blanket of nitrogen. After removal of the ether, the product (78 g, 85 percent yield) is distilled in vacuum, b.p. 121°–123° C/5 mm.

EXAMPLE 27

4-(Diphenylphosphinyl)phenyl Silsequixane

4-Chlorophenyl trichlorosilane (24.3 g, 0.1 mol) is hydrolyzed with 200 ml of 10 percent aqueous hydrochloric acid at 20° C for 4 hours. The white solid (16 g) is collected by filtration. It melts above 300° C. and is insoluble in all common organic solvents and in water.

The 4-chlorophenyl silisesquioxane prepared as above is charged together with lithium (1.4 g, 0.2 g atom) and 250 ml dry tetrahydrofuran to a flask and heated at reflux for 16 hours. This is cooled to 25° C and diphenylphosphinous chloride (8.8 g, 0.04 mol) dissolved in 50 ml tetrahydrofuran is dropped in during 1½ hours. The solution is refluxed 2 hours more. At this state, a homogeneous solution is obtained. The solvent is removed in vacuum leaving 28 grams of white solid, soluble in ethanol and tetrahydrofuran, but insoluble in water and common organic solvents. The solid is separated from occluded lithium chloride by repeated solution in tetrahydrofuran and precipitation with n-hexane, weight 16 g, m.p. >300° C. The infrared spectrum of this solid shows absorption bands at 3.27, 6.29, and 6.70 microns (aromatic), 12.25 microns (p-substituted aromatic), 13.23, 13.79, and 14.44 microns (mono-substituted aromatic), 8.80 microns (Si-phenyl), and 9.17 microns (Si—O). The elemental analysis was: Calculated for $C_{18}H_{14}SiPO_{3/2}$: C = 68.99; H = 4.50; Si = 8.96; P = 9.88. Found: C = 66.07; H = 4.77; P = 9.92.

Example 28

Coupling of p-Halophenyl Triethoxysilane and p-Halophenyl Diphenylphosphine A. With Lithium Metal. To a suspension of (1.44 g, 0.2 g atom) lithium powder of 150 A particle size in 50 ml anhydrous tetrahydrofuran under nitrogen and cooled to 0°, 27.5 g (0.1 mol) of p-chlorophenyl triethoxysilane dissolved in dry tetrahydrofuran is added during 2 hours. The solution turns very dark red as the lithium is dissolved. p-Chlorophenyl diphenylphosphine (29.7 g, 0.1 mol) dissolved in tetrahydrofuran and anhydrous cuprous chloride (100 mg, 0.001 mol) are added and the mixture heated at reflux temperature for 2 hours. The solution remains dark colored but on standing, lightened. Precipitated salts (8 grams) are filtered off and washed with benzene. The solvents are removed by concentration in vacuum leaving a tan syrup containing a small amount of solid. The liquid is redissolved in benzene, the solids removed by filtration and the solution reconcentrated to 30 grams of yellow oil. Gas-liquid and thin-layer chromatography showed the oil to consist of a small amount of unreacted chlorosilane and chlorophosphine and a major amount of a higher-boiling component. The volatile components are removed by distillation under high vacuum leaving a tan solid (24 grams) insoluble in most solvents. No chlorine is present. The H'NMR, delta (DMF-d7): 1.10 ($t$, 9H); 3.74 ($q$, 6H); 6.9–8.0 ($m$, 18H), is expected for the structure $(C_6H_5)_2PC_6H_4.C_6H_4Si(OC_2H_5)_3$.

B. With Copper Powder. A mixture of 4-bromophenyl triethoxysilane (14.9 g, 0.0467 mol), 4-bromophenyl diphenylphosphine (10.3 g, 0.0302 mol) and copper powder (1.0 g) are heated at 250° C for 3 hours. During this time solid separated and is recovered by filtration (26 g) leaving 10 grams of light yellow liquid. The liquid contains 0.011 mol unreacted silane and 0.001 mol phosphine by gas-liquid chromatographic analysis. The solid is insoluble in common solvents but soluble in dimethylforamide. Copper is removed by filtration of the DMF solution. Thin-layer chromatography (ethyl acetate) shows the solid to be mainly one component, $R_f = 0.16$ with small amounts of lighter materials, $R_f = 0.4, 0.6, 0.97$. The H'NMR of the material having $R_f = 0.16$ recovered from the chromatography is similar to the material above.

EXAMPLE 29

Palladium Complex of Diphenylphosphinylethylsilsesquioxane

The 5P:1 Pd complex is prepared by refluxing a solution of 0.5363 grams (1.56 mol) of sodium chloropalladite tetrahydrate in 80 ml of anhydrous ethanol with 2.003 g of the polymer having a phosphorous content of 3.56 meq./gram, for 3 hours. After cooling, the solids are filtered on a Buchner filter, washed with ethanol, and dried. Recovery 2.2516 grams, of light lemon-yellow solid.

EXAMPLE 30

Platinum Complex of Diphenylphosphinylethylsilsequioxane

A solution of 0.890 grams of sodium bisulfite in 10 ml distilled water is added to a solution of 0.7388 grams of chloroplatinic acid hexahydrate in 40 ml of anhydrous ethanol. The solution is warmed to expel sulfur dioxide. The polymer, containing 3.56 meq.P/gram (2.0046 grams suspended in 40 ml ethanol) is then added and the mixture refluxed 3 hours. After cooling, the solids are recovered by filtration, washed twice with 6 ml portions of distilled water, and dried. Recovery 2.4970 grams of light orange-yellow solid, the 5P:1 Pt complex.

EXAMPLE 31

Use of the Platinum Complex of Diphenylphosphinylethylsilsesquioxane as a Silylation Catalyst A mixture of allyl chloride (0.05 mol, 6.72 g) and the catalyst 2.4 mg., (1.66 millimol) is placed in a 1 inch × 8 inch heavywalled glass test tube and capped with a pressure seal. The tube is shaken in a 70° C water bath for 8 hours. A sample of the liquid is withdrawn and analyzed for 3-chloropropyltrichlorosilane, which is found to be present. Its presence is confirmed by spiking the sample with authentic material and co-chromatographing the mixture. The product liquid is completely removed from the solid catalyst and replaced with a fresh mixture of allyl chloride and trichlorosilane and the experiment is repeated. Again, after 4 hours reaction, 3-chloropropyltrichlorosilane is observed in the liquid. The liquid is again removed, replaced with fresh reactants and the experiment run through two additional cycles. Each time the condensation product, 3-chloropropyl trichlorosilane is produced. This demonstrates that the solid is catalytic for silylation, and not soluble in the reactants or in the products.

EXAMPLE 32

Use of the Palladium Complex of Diphenylphosphinylethylsilsesquioxane as a Catalyst for Octadienol Synthesis A mixture of the catalyst (0.309 g, containing 220 m mols of palladium) 182.5 mg of the diphenylphospinylethylsilsesquioxane, 5.0 grams (108.5 m mols) of ethanol, 1.0 ml (55.5 m mols) of distilled water, and 3.0 grams (55.5 m mols) of 1,3-butadiene is placed in a 1 inch × 8 inch heavy-walled, glass test tube and capped with a pressure seal. The tube is shaken in a 70° C. water bath for 2 hours. Analysis by gas-liquid chromatography shows the presence of 2,7-octadienol-1 and ethyl 2,7-octadienyl ether. The liquid is removed, replaced with fresh reactants, and the experiment is rerun using the same catalyst. Again, the same products are produced.

Abbreviations used in the foregoing examples have the following conventional meanings: g. = gram; b.p. = boiling point; mm. = millimeter(s); H'NMR = proton nuclear magnetic resonance spectroscopy; $s$ = singlet; $d$ = doublet $t$ = triplet; $q$ = quintet; $m$ = multiplet; meq. = millequivalents; ml = milliliter; $J$ = coupling constant; cps = cycles per second; $D$ = deuterium; SE-30 = a silicone gum rubber; Chromosorb W = a flux-calcined diatomaceous silicious absorbent produced by the Johns-Manville Corp.

I Claim;

1. A catalyst composition consisting essentially of a non-linear polymer consisting essentially of a recurring unit having the following structural formula:

$$(R^2)_2P-R^1-Si-O_{3/2}$$

wherein $R^1$ is an unsubstituted or substituted straight or branched chain divalent saturated alkylene radical having 1 to 10 carbon atoms or an unsubstituted or substituted divalent aryl radical having 1 to 3 benzene rings wherein the substituents for the alkylene radical can be halogen or a phenyl radical and the substituents for the aryl radical can be halogen or straight or branched chain saturated alkyl radicals having 1 to 5 carbon atoms; and $R^2$ is an unsubstituted or substituted straight or branched chain or cyclic monovalent saturated alkyl radical having 1 to 10 carbon atoms or an unsubstituted or substituted monovalent aryl radical having 1 to 3 benzene rings wherein the substituents for the alkyl radical can be halogen or a phenyl radical and the substituents for the aryl radical can be halogen or straight or branched chain saturated alkyl radicals having 1 to 5 carbon atoms; and wherein each phosphorous atom in the polymer is coordinated with a platinum or palladium metal atom having a zero or positive charge, each positively charged metal atom having a sufficient number of negatively charged organic or inorganic radicals, devoid of functional groups, attached thereto, to satisfy the valence of said transition metal atom, and wherein the radicals are selected from the group consisting of halogens; nitrates; sulfates; straight chain alkoxy or acyloxy radicals having 1 to 10 carbon atoms; and aryloxy radicals having 1 to 3 benzene rings.

2. The catalyst composition defined in claim 1 wherein the polymer defined therein contains 1 to 20 mol percent of cross-linking units having the following structural formula:

$$R^3O-Si-O_{3/2}$$

wherein $R^3$ is defined in the same manner as $R^2$, said units being randomly interspersed among the units of the polymer to provide cross-linking.

3. The catalyst composition defined in claim 2 containing 5 to 15 mol percent of said cross-linking units.

4. The catalyst composition defined in claim 1 wherein $R^1$ is an alkylene radical having 1 to 5 carbon atoms or an unchlorinated phenylene or diphenylene radical; and $R^2$ is an alkyl radical having 1 to 5 carbon atoms or an unchlorinated or chlorinated phenyl or diphenyl radical.

5. The catalyst composition defined in claim 4 wherein the negatively charged radical is chloride.

* * * * *

UNITED STATES PATENT OFFICE
CERTIFICATE OF CORRECTION

Patent No. 3,987,009      Dated October 19, 1976

Inventor(s) F.G. Young

It is certified that error appears in the above-identified patent and that said Letters Patent are hereby corrected as shown below:

In column 14, line 28, correct "96°C" to read -- 95°C --

In column 16, line 46, correct "-20°C" to read -- -10°C --

In column 18, line 52, delete "bH" and insert therefor -- 6H --

In column 20, line 4, correct "chromatography" to read

-- chromatograph --

Signed and Sealed this

Twenty-eighth Day of June 1977

[SEAL]

*Attest:*

RUTH C. MASON
*Attesting Officer*

C. MARSHALL DANN
*Commissioner of Patents and Trademarks*